United States Patent [19]

Dueber et al.

[11] Patent Number: 4,477,556

[45] Date of Patent: Oct. 16, 1984

[54] ACIDIC O-NITROAROMATICS AS PHOTOINHIBITORS OF POLYMERIZATION IN POSITIVE WORKING FILMS

[75] Inventors: Thomas E. Dueber; William J. Nebe, both of Wilmington, Del.

[73] Assignee: E. I. Du Pont de Nemours and Company, Wilmington, Del.

[21] Appl. No.: 409,096

[22] Filed: Aug. 18, 1982

[51] Int. Cl.³ .................. G03C 2/68; G03C 5/00; C07C 79/46
[52] U.S. Cl. .................. 430/281; 260/413; 549/351; 549/358; 549/439; 549/451; 560/108; 560/109; 560/110; 560/138; 560/139; 560/140; 560/141; 560/142; 562/426; 562/427; 562/432; 562/434; 562/435; 562/437; 562/438
[58] Field of Search .............. 562/434, 435, 437, 438, 562/436; 549/439; 260/413 Q, 413 R; 430/281, 917, 919; 204/159.18

[56] References Cited

U.S. PATENT DOCUMENTS

| | | | |
|---|---|---|---|
| 3,458,311 | 7/1969 | Alles | 430/300 |
| 3,674,836 | 7/1972 | Creger | 260/413 R |
| 3,886,284 | 5/1975 | Merianos et al. | 549/439 |
| 3,895,952 | 7/1975 | Schlesinger | 204/159.18 |
| 4,013,708 | 3/1977 | Haas et al. | 260/413 Q |
| 4,098,816 | 7/1978 | Thorne et al. | 562/435 |
| 4,162,162 | 7/1979 | Dueber | 430/281 |
| 4,198,242 | 4/1980 | Pazos | 430/301 |
| 4,273,857 | 6/1981 | Leberzammer et al. | 204/159.16 |
| 4,341,860 | 7/1982 | Sysak | 430/277 |

*Primary Examiner*—Natalie Trousof
*Assistant Examiner*—Patricia M. Scott

[57] ABSTRACT

A photopolymerizable coating composition comprising
(1) a nongaseous, ethylenically unsaturated, polymerizable compound,
(2) a specified acidic o-nitroaromatic compound, and
(3) an organic, radiation-sensitive, free-radical generating system which is useful for making a positive or negative polymeric image on a substrate.

11 Claims, No Drawings

ACIDIC O-NITROAROMATICS AS PHOTOINHIBITORS OF POLYMERIZATION IN POSITIVE WORKING FILMS

BACKGROUND OF THE INVENTION (1) Field of the Invention

This invention relates to photoinhibitors and their use in photopolymerizable compositions, and to methods of producing positive and negative polymeric images from these compositions.

(2) Description of the Prior Art

Recently polymeric imaging systems which provide a positive polymeric image have been developed. One such system is described by Pazos in U.S. Pat. No. 4,198,242. In this system
(a) a substrate is coated with a photopolymerizable composition containing
  (1) a nongaseous, ethylenically unsaturated, polymerizable compound,
  (2) 0.001 to 10 parts by weight per part of polymerizable compound of an organic, radiation-sensitive, free radical generating system, and
  (3) 0.004 to 0.7 parts by weight per part of polymerizable compound of a nitroaromatic compound, and
(b) the photopolymerizable coating is exposed through a process transparency to radiation, at least some of which has a wavelength less than 380 nm whereby the nitroaromatic compound is dissociated to a polymerization-inhibiting nitroso monomer in the radiation-struck areas, and
(c) a greater portion of the photopolymerizable coating is exposed to radiation substantially limited to wavelengths greater than 380 nm whereby a positive polymeric image is formed in the areas struck by the second radiation but not struck by the first imagewise radiation.

Although this system can produce excellent positive polymeric images, the photoinhibitor generally is not soluble in aqueous coating solutions and there is room for improvement in the stability of the latent image during hold times between the untraviolet and visible exposures.

SUMMARY OF THE INVENTION

This invention provides a novel group of photoinhibitors, along with a group of photopolymerizable compositions in which the photopolymerizable and photosensitive components consist essentially of
(a) a normally nongaseous, ethylenically unsaturated compound capable of addition polymerization by free-radical initiated chain propagation,
(b) about 0.004 to about 0.7 part by weight, per part of component (a), of an acidic o-nitroaromatic compound of the formula

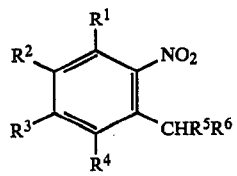

wherein
  $R^1=R^4=H$ or the residue of a second benzene ring as defined below; and at least one of $R_2$, $R_3$, $R_5$ or $R_6$ must have a carboxylic acid functionality as indicated below;
  $R^2$, $R^3$, alike or different, are H, OH, halogen, $NO_2$, alkyl of 1 to 18 carbons, alkoxy in which the alkyl is of 1 to 18 carbons, acyloxy of 2 to 7 carbons, aryl of 6 to 18 carbons, benzyl, halogen-substituted phenyl, polyether of 2 to 18 carbons and 2 to 10 oxygens, dialkylamino in which each alkyl is of 1 to 18 carbons, thioalkyl in which the alkyl is of 1-18 carbons, thioaryl in which the aryl os of 6 to 18 carbons, or $-O(CH_2)_xCO_2H$ or $(CH_2)_xCO_2H$ where $x=1$ to 12;
  $R^2$ and $R^3$, taken together, are $-OCH_2O-$ or $-O-(-CH_2CH_2O)-_q$ in which q is an integer from 1 to 5;
  or any two of $R^1$, $R^2$, $R^3$ and $R^4$, taken together, are the residue of a second benzene ring fused into the benzene nucleus, with the proviso that not more than one of $R^2$, $R^3$ is OH or $NO_2$;
  $R^5$ is H, a $C_1-C_{18}$ alkyl, OH, phenyl, or alkoxy in which the alkyl is of 1 to 18 carbons,
  $R^6$ is H; alkyl; phenyl; alkoxy in which the alkyl is of 1 to 18 carbons; aryloxy of 6 to 18 carbons, either unsubstituted or substituted with halogen, $C_1-C_6$ alkyl, $C_1-C_6$ alkoxy, or $-COOH$; $(CH_2)_xCO_2H$ where $x=1-12$ and $x\ne 2$ or 3 when $R_5$ is OH, with the proviso that only one of $R^5$ and $R^6$ is H; or
  $R^5$ and $R^6$ together are $=O$ or $-O-C_2H_4-O-$; with the proviso that carboxyl is excluded on the ring containing the nitro group and neither $R_5$ or $R_6$ is carboxyl.

(c) about 0.001 to about 10 parts by weight, per part of component (a), of an organic, radiation-sensitive, free-radical generating system which is activatable by actinic radiation that does not significantly rearrange the acidic o-nitroaromatic compound to an inhibitor of free-radical polymerization.

Preferably components (a), (b) and (c), in combination, comprise about 15-100% by weight of the photopolymerizable composition with a polymeric binder (d), filler, or other adjuvants comprising 0 to 85% by weight.

Photoinhibitor compounds (b) upon UV exposure from nitroso ($-N=O$) inhibitors of polymerization. Exposure in the visible (visible sensitizer or initiator is used) polymerizes the nonimaged areas, yielding positive images upon development. Advantages of the acidic o-nitroaromatic compounds of this invention as photoinhibitors are:
  (a) Coating from water (dilute ammonium hydroxide) is possible, and
  (b) better latent image stability is obtained than with the currently used photoinhibitor.

Positive polymeric images are produced on a substrate by the process which comprises
  (1) coating the substrate with the above photopolymerizable composition,
  (2) imagewise exposing a portion of the photopolymerizable coating through an image-bearing transparency to radiation, at least about 20% of which has a wavelength of about 200 to about 380 nm, thereby rearranging at least some of the acidic o-nitroaromatic compound to polymerization-inhibiting nitroaoaromatic compound, and (3) subjecting the coating to a second exposure, whereby a greater portion of the coating, including the portion exposed during the imagewise exposure, is exposed to radiation substantially limited to wavelengths greater than about 380 nm, whereby a positive polymeric image is formed in the areas exposed during the second exposure, but not exposed during the imagewise exposure. The image formed in step (3) is developed by removing the unpolymerized portion of the photopolymerizable coating in the areas exposed to the imagewise exposure radiation, or by differential adhesion of a pigment toner to the saie unpolymerized portion of the coating.

Negative polymeric images are produced on a substrate by the process which comprises
(1) coating the substrate with the above photopolymerizable composition, and
(2) imagewise exposing a portion of the photopolymerizable coating through an image-bearing transparency to radiation substantially limited to wavelengths greater than about 380 nm, whereby a negative polymeric image is formed in the areas exposed to the radiation.

DETAILED DESCRIPTION OF THE INVENTION

In a preferred embodiment the photoinhibitor has the formula

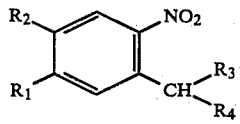

wherein at least one of $R_1$, $R_2$, $R_3$ and $R_4$ must have a carboxyl group as indicated below; $R_1$, $R_2$, alike or different, are selected from alkoxy in which the alkyl is of 1 to 12 carbons, and $(CH_2)_xCO_2H$ where $x=1$ to 12;

$R_1$ and $R_2$, taken together, are $-OCH_2O-$;

$R_3$ is selected from H, lower alkyl, OH, and alkoxy in which the alkyl portion is of 1 to 6 carbons;

$R_4$ is aryloxy of 6 carbons substituted with carboxyl, or $(CH_2)_xCO_2H$ where $x=2-12$, and $x\neq 2$ or 3 when $R_3$ is OH.

The nitroso compounds formed by irradiation of the acidic-o-nitroaromatic compounds described herein with short wavelength radiation interfere with the normal free-radical induced polymerization process. Thus, when using the shorter wavelength region of the spectrum in the presence of a nitrosoaromatic compound, an insufficient number of initiating and propagating free radicals is available, and polymerization does not occur. When a composition of this invention is exposed to radiation of wavelength greater than about 380 nm, the acidic o-nitroaromatic compound is relatively unaffected, and the photoinitiator system operates to produce initiating radicals. These radicals are able to effect chain propagation in the usual way and polymerization occurs.

Suitable polymerizable compounds for use as component (a) of the photopolymerizable coating compositions of this invention are normally nongaseous, ethylenically unsaturated compounds. By "normally nongaseous" is meant compounds which are not gases under atmospheric conditions. They are preferably monmeric, have a boiling point above 90° C. at normal atmosphere pressure, and contain at least one terminal ethylenic group, but most preferably contain 2-5 terminal ethylenic groups.

Suitable polymerizable compounds include unsaturated esters of polyols, particularly such esters of α-methylenecarboxylic acids, for example, ethylene glycol diacrylate, diethylene glycol diacrylate, glycerol diacrylate, glyceryl triacrylate, mannitol polyacrylate, sorbitol polyacrylates, ethylene glycol dimethacrylate, 1,3-propanediol dimethacrylate, 1,24-butanetriol trimethacrylate, 1,1,1-trimethylolpropane triacrylate, triethylene glycol diacrylate, 1,4-cyclohexanediol diacrylate, 1,4-benzenediol dimethacrylate, pentaerythritol di-, tri-, and tetramethacrylate, dipentaerythritol polyacrylate, pentaerythritol di-, tri-, and tetraacrylates, 1,3-propanediol diacrylate, 1,5-pentanediol dimethacrylate, the bis-acrylates and methacrylates of polyethylene glycols of molecular weight 200–4000, and the like; unsaturated amides, particularly those of α-methylenecarboxylic acids, and especially those of α,ω-diamines and oxygen-interrupted ω-diamines, such as methylene bis-acrylamide, methylene bis-methacrylamide, ethylene bis-methacrylamide, 1,6-hexamethylene bis-acrylamide, bis(γmethacrylamidopropoxy)-ethane and β-methacrylamidoethyl methacrylate; vinyl esters such as divinyl succinate, divinyl adipate, divinyl phthalate, divinyl terephthalate, divinyl benzene-1,3-disulfonate and divinyl butane-1,4-disulfonate; unsaturated aldehydes, such as hexadienal; and mixtures thereof.

A preferred group of the acidic o-nitroaromatic compounds of this invention are:

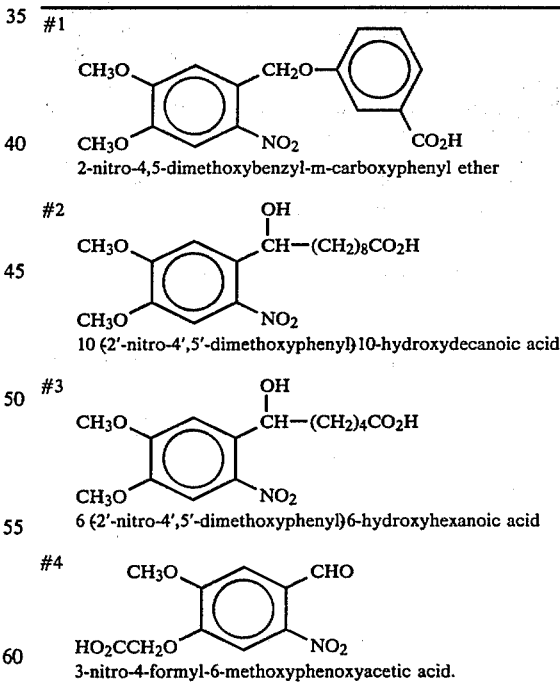

1 2-nitro-4,5-dimethoxybenzyl-m-carboxyphenyl ether

2 10 (2'-nitro-4',5'-dimethoxyphenyl)10-hydroxydecanoic acid

3 6 (2'-nitro-4',5'-dimethoxyphenyl)6-hydroxyhexanoic acid

4 3-nitro-4-formyl-6-methoxyphenoxyacetic acid.

The acidic o-nitroaromatic compounds are ordinarily employed in concentrations of about 0.004 to about 0.7 parts by weight per part of polymerizable compounds. The preferred amount in any specific case will depend upon the particular monomer/free-radical generating system employed. In general, the preferred amount of nitroaromatic compound is about 0.04 to about 0.15 parts by weight per part of polymerizable compound.

The third component which the photopolymerizable coating composition must contain in an organic, radiation-sensitive, free-radical generating system which initiates polymerization of th monomer and does not subsequently terminate the polymerization. The word "organic" is used here and in the claims to designate compounds which contain carbon, and one or more of oxygen, hydrogen, nitrogen, sulfur and halogen, but are free of metal.

The free-radical generating system absorbs actinic radiation with wavelengths within the range of about 200 to about 800 nm that does not significantly rearrange the acidic o-nitroaromatic compound to an inhibitor of free-radical polymerization. By "actinic radiation" is meant radiation which is operative to produce the free radicals necessary to initiate polymerization of the monomeric material. The free-radical generating system can comprise one or more compounds which directly furnish free radicals when activated by radiation. It can also comprise a plurality of compounds, one of which yields the free radicals after having been caused to do so by a sensitizer which is activated by the radiation. Preferably the free-radical generating system has at least one component having a radiation absorption band with a molar extinction coefficient of at least about 50 within a range greater than about 380-800 nm, and more preferably about 400-600 nm.

A large number of free-radical generating compounds can be utilized in the practice of this invention including aromatic ketones, benzoin ethers, quinones and 2,4,5-triarylimidazolyl dimers; such compounds are lised in U.S. Pat. No. 4,198,242, supra, at column 9, line 45 to column 10, line 14, which lines are incorporated herein by reference.

A preferred group of free-radical generating systems characterized by good efficiency includes those disclosed in U.S. Pat. No. 4,162,162 and U.S. Pat. No. 4341860 which are incorporated herein by reference. The concentration of the free-radical generating system is about 0.001 to about 10.0 parts by weight per part of polymerizable compound, and preferably about 0.01 to about 2.0 parts by weight.

In a preferred embodiment of the invention, one or more polymeric binders are present and the polymeric binder is selected so that the unexposed photopolymerizable coating is soluble in predominantly aqueous solutions, for exmple dilute aqueous alkaline solutions, but upon exposure to actinic radiation becomes relatively insoluble therein. Typically, polymers which satisfy these requirements are carboxylated polymers, for example vinyl addition polymers containing free carboxylic acid groups. In a particularly preferred embodiment of this invention the photopolymerizable compositions contain aqueous processable binder or binder combinations disclosed in U.S. Pat. No. 4,273,857, U.S. Pat. No. 4,293,635 and U.S. Pat. No. 3,458,311 which disclosures are incorporated herein by reference.

When a monomer/binder system is employed, the amount of polymeric binder present is about 10 to about 80% by weight based on the total solids content, and preferably about 25% to about 75%. Polymerizable compounds which contain only one site of ethylenic unsaturation are generally not satisfactory for use in a monomer/binder system. With certain polymers, it may be desirable to add a plasticizer to give flexibility to the resulting photopolymerizable layer and facilitate selective development.

The photopolymerizable compositions described herein may be coated on a wide variety of substrates. By "substrates" is meant any natural or synthetic support, preferably one which is capable of existing in a flexible or rigid film or sheet form. For example, the substrate could be a metal sheet or foil, a sheet or film of synthetic organic resin, cellulose paper, fiberboard, and the like, or a composite to two or more of these materials. Specific substrates include polyethylene terephthalate film, polyvinylidene chloride copolymer-coated oriented polyester film, nylon, glass, cellulose acetate film, andd the like. The substrate surfaces may be treated or untreated, e.g., by flame or electrostatic discharge, and may contain one or more sub or auxiliary coatings.

The compositions of the invention are exposed to radiation of wavelength in the 200-800 nm range. Suitable sources of such radiation, in addition to sunlight, include carbon arcs, mercury-vapor arcs, fluorescent lamps, electronic flash units, photographic-flood lamps, and lasers.

During the first exposure in preparing a positive polymer image, radiation having a wavelength of about 200 to about 380 nm is used, but it is not necessary that the wavelength be limited to this range. The radiation may have wavelengths over the entire range of about 200 to about 800 nm. In order to form an effective amount of inhibitor in the first exposure, at least about 20% of the radiation should be between about 200 and about 380 nm; and preferably at least about 30% of the radiation is within this range.

The radiation used during the second exposure should be substantially limited to wavelengths greater than about 380 nm, preferably about 380 to about 800 nm, and ideally about 400 to about 600 nm. During the second exposure, a greater portion of the coating, typically the entire coated area, is struck by radiation with the result that free radicals are generated and polymerization takes place in the areas struck by radiation during the second exposure but not during the first exposure.

Imagewise exposure, for example in preparing printing plates, is conveniently carried out by exposing a layer of the photoactive composition to radiaion through a "process transparency", that is, an image-bearing transparency consisting solely of areas substantially opague and substantially transparent to the radiation being used where the opaque areas are substantially of the same optical density; for example, a so-called line or halftone negative or positive. First exposure of a plate coated with the acidic o-nitroaromatic compound-containing photoactive composition to the full spectrum of a mercury-vapor lamp through a film negative causes rearrangement of the nitroacromatic compound to a nitrosoaromatic compound in the radiation-struck areas. These areas will become nonimage areas since no polymerization will be initiated in these areas.

Removal of the process transparency followed by a second exposure of the plate to radiation wavelengths substantially greater than about 380 nm causes polymerization to occur in the areas which were not struck by radiation during the first exposure. Radiation of this wavelength is insufficiently absorbed by the acidic o-nitroaromatic compound to rearrange it to a nitroso compound. Development of the doubly exposed plate with solvent washout removes the unpolymerized parts of the coating, leaving behind a polymeric replica of the original.

The same compositions used for the two-exposure positive-working applications described above may also be used to form negative polymeric images by the single exposure procedure. For this application, a layer of any photopolymerizable nitroaromatic compound-containing composition described above is exposed through an image-bearing transparency to radiation substantially limited to wavelengths above about 380 nm until polymer is formed in the exposed areas. Unpolymerized portions of the photopolymerizable layer are then removed by solvent washout, or any other removal method, to leave a negative polymeric image of the pattern of the transparency employed.

The photopolymerizable compositions of this invention have the very special advantage that the imagewise exposure of the positive-working process can be carried out using polyethylene terephthalate process transparencies. This is possible because the nitroaromatic compounds are sensitive to radiation of wavelength about 336 nm which is readily passed by polyethylene terephthalate film. Most of the previously known sources of nitroso inhibitors in positive-working photopolymerizable compositions have required activation by radiation having wavelengths below about 330 nm which is substantially screened out by polyethylene terephthalate film. Thus, the present invention is useful with the latest, and most preferred, image-bearing transparences.

The following examples further illustrate the compositions and methods of this invention. All parts and percentages are by weight unless otherwise specified.

EXAMPLE 1

Preparation of 2-nitro-4,5-dimethoxybenzyl alcohol 1011 g of 2-nitro-4,5-dimethoxybenzaldehyde in 10 l of ethanol with 94.8 ml water added was stirred, and a solution of 57 g sodium borohydride in 2 l absolute ethanol was added over 1 hour. The mixture was heated to 40° C. for 2.5 hours, cooled to 5° C. and the mixture filtered. The solid was washed with 4 l of cold 2B alcohol (denatured ethanol) and 8 l cold water, and dried in a 50° C. vacuum oven to yield 570 g, 56.5% yield.

Preparation of 2-nitro-4,5-dimethoxybenzyl chloride 570 g of 2-nitro-4,5-dimethoxybenzyl alcohol was added over 1 hour to 733 ml of thionyl chloride at 0° C. The solution was heated to 25° C. over 2 hours and to 50°–56° C. for 2 hours. The solution was cooled to 5° C. and the mixture was poured onto 12 l of ice water with stirring. The supernatant was poured off and the solid washed with water. The oily solid was blended with ice and water, filtered, and dried in a 40° C. vacuum oven to yield 535 g, 86.4% yield.

Preparation of 2-nitro-4,5-dimethoxybenzyl-m-carboxylphenyl ether 3 g m-hydroxybenzoic acid was added to a solution of 2.33 g sodium methoxide in 30 ml ethanol with stirring. After 10 minutes 5 g of benzyl chloride was added over 5 minutes, followed by 45 ml of absolute ethanol and the mixture heated to reflux at 78° C. for 4 hours. The reaction mixture was filtered hot. The solid was taken up in 500 ml water, acidified with 10% aqueous hydrochloric acid, and the solid collected by filtration, washed with hot water, and the yellow solid recrystallized from 300 ml of absolute ethanol to yield 2.6 g of product.

EXAMPLE 2

Preparation of 10-(3',4'-dimethoxyphenyl)-decanoic-10-one acid

To 67 g of veratrole in 230 ml 1,1,2,2-tetrachloroethane (TCE) and 70 ml nitrobenzene was added, with stirring under nitrogen 147 g of anhydrous aluminum chloride followed by the addition of a solution of 90 g polysebacic anhydride in 270 ml TCE over 35 minutes at 0° C. The reaction mixture was stirred in an ice bath for 4 hours and allowed to stand overnight. The viscous red mass was added to a stirred solution of 170 ml water, 117 ml conc. HCl, and 500 g ice. The mixture was filtered and the solid was washed three times with 200 ml methylene chloride and water. The filtrate was separated and the water layer washed with methylene chloride. The methylene chloride layers were combined and shaken with 5% potassium carbonate solution. The resulting emulsion was broken up with the addition of acetone. A total of 4 carbonate washes of 270 ml each was used with acetone added with each extraction. The water layers were combined and stirred in an ice bath as conc. HCl was added until the pH was approximately 2. The while solid product was filtered off the next day, washed with water and air dried to give 50 g after 50° C. vacuum oven drying.

Preparation of 10-(2'-nitro-4',5'-dimethoxyphenyl)-decanoic-10-one acid 25 g of 10-(3',4-dimethoxyphenyl)-decanoic-10-one acid was added over 45 min to 175 ml conc. nitric acid at 10°–15° C. The product started precipitating out after 80% addition. The addition of 20 ml conc. nitric acid did not give a solution. The reaction mixture was stirred 20 min with a temperature of 18° C. reached, and was poured into 680 ml ice water, filtered, and the solid washed until the filtrate was neutral. The solid was stirred in 1.3 l boiling water 2 times and collected by filtering while the mixture was hot. The solid was vacuum oven-dried at 50° C. to yield 19 g, 66% yield.

Preparation of 10-(2'-nitro-4',5'-dimethoxyphenyl)-10-hydroxydecanoic acid

To a rapidly stirred solution of 8.33 g potassium carbonate 1.5 hydrate in 330 ml water was added 18.5 g of the nitrophenyl ketone. 2.5 g of potassium carbonate was added to make a clear solution. A solution of 2.36 g sodium borohydride in 50 ml water was added over 5 min. The mixture was heated to 45° for one hour, cooled to room temperature over 2 hours, and shaken with 200 ml ether. The layers were separated and the water layer stirred as a solution of 8% aqueous HCl was added until the solution was a pH of 2-3. An orange solid was collected by filtration, blended in ice water, filtered, washed with water and vacuum oven dried at 60° C. to yield 18 g, 95% yield.

EXAMPLE 3

Preparation of 6-(3'-,4'-dimethoxyphenyl)-hexanoic-6-one acid

The same procedure was followed as for the decanoic acid derivative except no acetone was required to separate the layers. 87 g veratrole and 87 polyadipic anhydride gave 44 g of product.

Preparation of 6-(2'-nitro-4'-,5'-dimethoxyphenyl)-hexanoic-6-one acid

The same procedure was followed as for the decanoic acid derivative. The product stays in solution in the nitric acid for this material. 20 g of starting material gave 16 g, 69% yield.

Preparation of 6-(2'-nitro-4',5'-dimethoxyphenyl)-6-hydroxyhexanoic acid

The same procedure was used as for the decanoic acid derivative. 10 g of nitrophenyl ketone gave 6 g of product.

EXAMPLE 4

Preparation of 2-methoxy-4-formyl phenoxyacetic acid

A solution of 80 g sodium hydroxide in 200 ml water was added to a mixture of 152 g of vanillin, 95 g chloroacetic acid, and 800 ml water with stirring. The mixture was heated to reflux 65 hours, cooled to room temperature, acidified with 70 ml conc. HCl, and the product collected by filtration. The solid was washed with 2 l of distilled water and dried to give 120 g, 57% yield.

Preparation of 3-nitro-4-formyl-6-methoxyphenoxyacetic acid 10 g of the phenoxyacetic acid was added to a mixture of 200 ml glacial acetic acid and 50 ml fuming nitric acid and the reaction mixture stirred at RT for 18 hours. The mixture was filtered and the filtrate was poured onto a mixture of 300 g ice and 200 ml water. The solid was collected by filtration, washed with cold water and dried in a vacuum oven to yield 6 g, 49% yield.

EXAMPLES 5-8

Litho Plate Application

Coating solutions were made up of the compositions given in Tables I and II. The solutions were coated onto 0.001 inch (0.0025 cm) polyethylene terephthalate film sheet, air dried, and laminated onto moistened anodized aluminum. To modulate exposure a $\sqrt[3]{2}$ stepwedge target was placed over the film which was then contacted in a vacuum frame. Exposures were made with a 2000 watt mercury photopolymer Addalux lamp at a distance of 38 inches (96.5 cm) using a Berkey "Ascor" 1601-40 light source. The first inhibitor-forming UV exposure was made with the full spectral output of the source. A part of the plate was kept from exposure with a piece of black polyethylene.

After the first exposure the $\sqrt[3]{2}$ stepwedge was moved to the unexposed area hidden from light during the UV exposure and a UV filter placed over the whole plate and given a visible, polymerization exposure. The plate was developed in a solution of 84 g potassium carbonate 1.5 hydrate, 5 g potassium bicarbonate, and 1536 g distilled water at 20° C. for 15 sec, followed by a 40° C., 40 psi (2.81 kg/sq cm) spray water rinse. The aluminum in the washout areas was cleanly uncovered and did not accept ink. In the portion of the plate receiving only a single imaging exposure of radiation substantially limited to wavelengths greater than about 380 nm, the unexposed areas were washed away to produce a reverse or negative image of the stepwedge. The inked plate was useful as an offset litho plate and the examples demonstrate that both positive and negative images can be obtained on the same plate depending on exposure conditions. The UV filter was prepared from a solution of 720 g of cellulose acetate butyrate, 320 g ethyl Cellosolve, and 80 g of a UV absorber, 2,2'-dihydroxy-4-methoxybenzophenone, which was coated on resin-subbed polyethylene terephthalate film to a thickness of 0.00095 inch (0.024 mm).

TABLE I

| Stock Solution | |
|---|---|
| Component | |
| Methylene chloride | 865 |
| Methanol | 36 |
| Terpolymer of ethyl acrylate (71), methyl methacrylate (17), acrylic acid (12); $MW_w = 150 M$ | 3 |
| Pentapolymer of octylacrylamide (40), methyl methacrylate (30), acrylic acid (16), hydroxypropyl methacrylate (6) and t-butylaminoethyl methacrylate (4); acid #118, $MW_w = 50 M$, $Tg \sim 120°$ C. | 61 |
| Trimethylolpropanetriacrylate | 14 |
| Triethyleneglycol dimethacrylate | 14 |
| 3[(1-ethyl-1,2,3,4-tetrahydro-6-quinolinyl)-methylene]-4-chromanone | 0.5 |
| bis[2-o-chlorophenyl-4,5-diphenyl]imidazole | 3 |
| 1,4,4-trimethyl-2,3-diazabicyclo[3 · 2 · 2]non-2-ene-N,N'—dioxide | 0.05 |
| Victoria green dye | 0.05 |
| Leuco crystal violet | 0.5 |

TABLE II

| Ex.[1] | Photo-Inhibitor | Exposures UV[3] | (units) Visible[4] | $\sqrt[3]{2}$ Stepwedge +[5] | Image −[6] |
|---|---|---|---|---|---|
| 5[2] | 1 | 50 | 50 | 3 | 14 |
| 6 | 2 | 50 | 50 | 1 | 14 |
| 7 | 3 | 50 | 50 | 4 | 14 |
| 8 | 4 | 100 | 100 | 5 | 12 |

[1]0.18 g photoinhibitor of Examples 5-8 added to 51.56 g aliquots of the stock solution of Table I.
[2]Coating weight 62 mg/dm².
[3]Full spectrum exposure forms inhibitor.
[4]Polymerization, visible exposure
[5]# unpolymerized, completely washed out steps.
[6]# polymerized steps from single, polymerization (visible) exposure. (The number of polymerized steps gives a relative comparison of the photopolymerization speed in the presence of the acidic o-nitroaromatic compound).

EXAMPLE 9

Litho Film Application

Black and clear coating solutions were made up of aqueous and organic parts with compositions given in Tables III and IV. The two parts of each coating solution were combined and emulsified in a Waring blender for 5 minutes at 70 volts. Afterwards 3.6 ml of a 5% aqueous solution of fluorocarbon surfactant

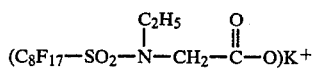

was added. The black layer emulsion was coated on resin-subbed polyethylene terephthalate with a 2 mil knife and dried with a hot air gun. The clear layer emulsion was diluted to 10% solids with distilled water and coated on the black film with a 2 mil knife. The coating was dried with a hot air gun and for 7 min in a 95°-100° C. oven and a polyethylene terephthalate cover sheet was laminated thereto. The image element is spray developed at 85° F. (29.4° C.) with a developer composed of 840 g $K_2CO_3$, 50 g $KHCO_3$ and 16 liters water in a Crona-Lite ® Model II processor manufactured by E. I. duPont de Nemours and Company, Wilmington, DE and rinsed by a 100° F. (about 38.0° C.) spray of water at 105 psi (7.38 kg/cm²). A UV imagewise exposure of 140 units (28 sec) was made with a 4 Kw pulsed xenon source 60 inches (152.4 cm) from the vacuum frame. This exposure was followed by a visible exposure of 1,100 units (220 sec) with a UV filter of the same composition as the one used for Examples 5-8 using the same source. The resulting image after development gave a positive image that gave excellent image quality over the tonal range of 2-98% dots, 150 lines/inch (59 lines/cm).

TABLE III
Black Pigmented Coating Solution

| Aqueous Part | Amount |
|---|---|
| Distilled water | 116 g |
| Photoinhibitor 2 | 2 g |
| Conc. ammonium hydroxide | 0.4 ml |
| Acrysol ® 1-94 acrylate resin, a product of Rohm & Haas Company | 43 g |
| Octylphenoxy polyethoxy ethanol (MW 646) (10% aqueous (solution) | 6 g |
| 25% ammoniacal solution of a roll-milled dispersion of 45% carbon black in a terpolymer of 56% ethyl acrylate, 37% methyl methacrylate and 7% acrylic acid; $MW_w = 260,000$, acid #76-85 | 70 g |
| A zinc complex solution prepared by dissolving 25 g ammonium carbonate in 143 g distilled water, adding 14 g zinc oxide, with stirring followed by the addition of 17 g conc. ammonium hydroxide | 4 g |
| Organic Part | |
| Methylene chloride | 15 g |
| Tetraethylene glycol dimethacrylate | 2 g |
| Trimethylolpropanetriacrylate | 2 g |
| 3[(1-ethyl-1,2,3,4-tetrahydro-6-quinolinyl)methylene]-4-chromanone | 0.2 g |
| bis(2-o-chlorophenyl-4,5-diphenyl-imidazole) | 1 g |
| bis(2-o-chlorophenyl-4,5-bis(m-methoxyphenyl)-imidazole | 1 g |
| 1,4,4-trimethyl-2,3-diazabicyclo-[3 · 2 · 2]non-2-ene-N,N'—dioxide | 0.02 g |

TABLE II
Clear Coating Solution

| Aqueous Part | Amount |
|---|---|
| Distilled water | 132 g |
| Photoinhibitor 2 | 2 g |
| Conc. ammonium hydroxide | 0.4 ml |
| Acrysol ® 1-94 | 75 g |
| Misco AC-392 polyethylene wax/water dispersion Misco Products Co., Reading, PA | 20 g |
| Triton ® X-100 (10% aqueous (solution) | 6 g |
| Zinc complex solution of Table III | 7 g |
| Organic Part | |
| Methylene chloride | 15 g |
| Tetraethylene glycol dimethacrylate | 2 g |
| Trimethylolpropanetriacrylate | 2 g |
| 3[(1-ethyl-1,2,3,4-tetrahydro-6-quinolinyl)methylene]-4-chromanone | 0.2 g |
| bis(2-o-chlorophenyl-4,5-diphenyl-imidazole) | 1 g |
| bis(2-o-chlorophenyl-4,5-bis(m-methoxyphenyl)-imidazole | 1 g |
| 1,4,4-trimethyl-2,3-diazabicyclo- | 0.02 g |

TABLE II-continued
Clear Coating Solution

| Aqueous Part | Amount |
|---|---|
| [3 · 2 · 2]non-2-ene-N,N'—dioxide | |

We claim:

1. An acidic o-nitroaromatic compound of the formula

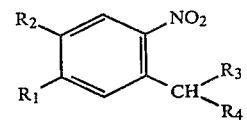

wherein at least on of $R_1$, $R_2$, $R_3$ or $R_4$ must have a carboxyl group as indicated below;

$R_1$, $R_2$, alike or different, are selected from alkoxy in which the alkyl is of 1 to 12 carbons, and $-(CH_2)_X CO_2H$ where $x = 1$ to 12;

$R_1$ and $R_2$, taken together, are $-OCH_2O-$, $R_3$ is selected from H, lower alkyl, OH, and alkoxy in which the alkyl portion is of 1 to 6 carbons;

$R_4$ is aryloxy of 6 carbons substituted with carboxyl, or $-(CH_2)_X CO_2H$ where $x = 2$ to 12, and $x \neq 2$ or 3 when $R_3$ is OH.

2.

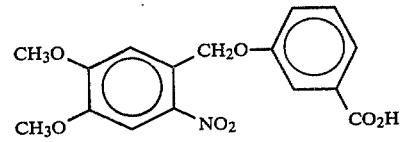

2-nitro-4,5-dimethoxybenzyl-m-carboxyphenyl ether

3.

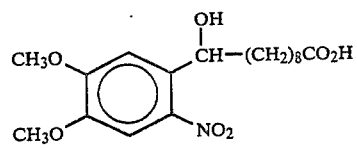

10-(2'-nitro-4',5'-dimethoxyphenyl)10-hydroxydecanoic acid

4.

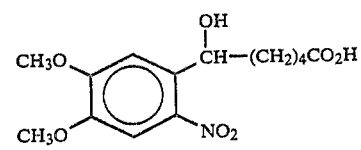

6-(2'-nitro-4',5'-dimethoxyphenyl)-6-hydroxyhexanoic acid

5.

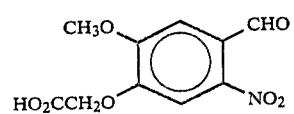

3-nitro-4-formyl-6-methoxyphenoxyacetic acid

6. A photopolymerizable composition which consists essentially of
   (a) a normally nongaseous, ethylenically unsaturated compound capable of addition polymerization by free-radical initiated chain propagation,
   (b) about 0.004 to about 0.7 parts by weight, per part of component (a), of the acidic o-nitroaromatic compound of claim 2, 3, 4, 5, or 6
   (c) about 0.001 to about 10 parts by weight, per part of component (a), of organic, radiation-sensitive, free-radical generating system, activatable by actinic radiation that does not significantly rearrange the acidic o-nitroaromatic compound to an inhibitor of free-radial polymerization.
   (d) 0 to 85% by weight of the total composition of a polymeric binder.

7. A photographic film composed of the composition of claim 6 coated upon a support.

8. A process for producing a positive polymeric image on a substrate which comprises
   (1) coating the substrate with the photopolymerizable composition of claim 6,
   (2) imagewise exposing a portion of the photopolymerizable coating through an image-bearing transparency to radiation, at least about 20% of which has a wavelength of about 200 to about 380 nm, thereby rearranging at least some of the acidic o-nitroaromatic compound to polymerization-inhibiting nitrosoaromatic compound, and
   (3) subjecting the coating to a second exposure whereby a greater portion of the coating, including the portion exposed during the imagewise exposure, is exposed to radiation substantially limited to wavelengths greater than about 38 nm, whereby a positive polymeric image is formed in the areas exposed during the second exposure, but not exposed during the imagewise exposure.

9. The process of claim 8 wherein the image formed in step (3) is developed by removing the unpolymerized portion of the photopolymerizable coating in the areas exposed to the imagewise exposure radiation, or by differential adhesion of a pigment toner to the said unpolymerized portion of the coating.

10. A process for producing negative polymeric images on a substrate, which comprises
    (1) coating the substrate with the photopolymerizable composition of claim 6, and
    (2) imagewise exposing a portion of the photopolymerizable coating through an image-bearing transparency to radiation substantially limited to wavelengths greater than about 380 nm, whereby a negative polymeric image is formed in the areas exposed to the radiation.

11. The process of claim 10 wherein the image formed in step (2) is developed by removing the unpolymerized portion of the photopolymerizable coating in the areas exposed to the imagewise exposure radiation, or by differential adhesion of a pigment toner to the said unpolymerized portion of the coating.

* * * * *

UNITED STATES PATENT AND TRADEMARK OFFICE
CERTIFICATE OF CORRECTION

PATENT NO. : 4,477,556
DATED : October 16, 1984
INVENTOR(S) : Thomas Eugene Dueber and William John Nebe It is certified that error appears in the above—identified patent and that said Letters Patent is hereby corrected as shown below:

| Column | Line | |
|---|---|---|
| 12 | 22 | "$-(CH_2)XCO_2H$" should be -- $-(CH_2)_xCO_2H$ --. |
| 12 | 27 | "$-(CH_2)XCO_2H$" should be -- $-(CH_2)_xCO_2H$ --. |
| 12 | 38 | "2-nitro-4,5-dimethoxybenzyl-m-carboxyphenyl ether" should be -- 2-nitro-4,5-dimethoxybenzyl-$\underline{m}$-carboxyphenyl ether --. |
| 14 | 5 | "38 nm" should be -- 380 nm --. |

Signed and Sealed this

Twenty-fifth Day of June 1985

[SEAL]

Attest:

Attesting Officer

DONALD J. QUIGG

Acting Commissioner of Patents and Trademarks